(12) United States Patent
Battle et al.

(10) Patent No.: US 8,285,826 B2
(45) Date of Patent: Oct. 9, 2012

(54) GRID COMPUTING ON RADIOLOGY NETWORK

(75) Inventors: Xavier Battle, Oak Park, IL (US); Joseph Fang, Barrington, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2073 days.

(21) Appl. No.: 10/880,112

(22) Filed: Jun. 29, 2004

(65) Prior Publication Data

US 2005/0288569 A1 Dec. 29, 2005

(51) Int. Cl.
*G06F 15/173* (2006.01)

(52) U.S. Cl. ........ 709/223; 709/241; 709/218; 709/227; 709/228

(58) Field of Classification Search .................. 709/223, 709/241, 218, 227, 228
See application file for complete search history.

(56) References Cited

U.S. PATENT DOCUMENTS

| | | | |
|---|---|---|---|
| 6,269,408 B1 * | 7/2001 | Berliner | 719/324 |
| 6,587,598 B1 * | 7/2003 | Devillers et al. | 382/284 |
| 7,218,766 B2 * | 5/2007 | Eberhard et al. | 382/132 |
| 2004/0249314 A1 * | 12/2004 | Salla et al. | 600/595 |
| 2005/0060202 A1 * | 3/2005 | Taylor et al. | 705/2 |
| 2005/0078861 A1 * | 4/2005 | Usikov | 382/131 |
| 2005/0213832 A1 * | 9/2005 | Schofield et al. | 382/240 |
| 2006/0241968 A1 * | 10/2006 | Hollebeek | 705/2 |
| 2007/0103984 A1 * | 5/2007 | Kavuri et al. | 365/185.17 |
| 2008/0008401 A1 * | 1/2008 | Zhu et al. | 382/294 |
| 2010/0280321 A1 * | 11/2010 | Modell | 600/160 |

* cited by examiner

*Primary Examiner* — Lan-Dai T Truong
(74) *Attorney, Agent, or Firm* — Peter Kendall

(57) ABSTRACT

A grid computing system and method is provided for medical data processing. The grid computing system comprises a software infrastructure, and an imaging device capable of interfacing with the software infrastructure over a distributed electronic network. Also included is a plurality of CPUs capable of interfacing with the software infrastructure over the network. The performance of the plurality of CPUs is dependent on balancing load. A large medical dataset is split onto several processing nodes of the plurality of CPUs, respectively, such that performance and power is increased. In the grid computing method, a grid is limited to a nuclear medicine or radiology network. A tight and easy configuration management of computing nodes, and a tight load balancing between standardized nodes are provided. An existing network of CPUs is utilized, such that the greatest benefit is provided at the lowest cost.

15 Claims, 2 Drawing Sheets

GRID COMPUTING ON RADIOLOGY NETWORK

BACKGROUND OF THE INVENTION

1. Field of the Invention

The present invention relates generally to medical imaging and, more particularly, to a system and method of processing medical images.

2. Description of the Background Art

Medical imaging is one of the most useful diagnostic tools available in modern medicine. Medical imaging allows medical personnel to non-intrusively look into a living body in order to detect and assess many types of injuries, diseases, conditions, etc. Medical imaging allows doctors and technicians to more easily and correctly make a diagnosis, decide on a treatment, prescribe medication, perform surgery or other treatments, etc.

There are medical imaging processes of many types and for many different purposes, situations, or uses. They commonly share the ability to create an image of a bodily region of a patient, and can do so non-invasively. Examples of some common medical imaging types are nuclear imaging, magnetic resonance imaging (MRI), ultrasound, X-rays, tomography of various types, etc. Using these or other imaging types and associated machines, an image or series of images may be captured. Other devices may then be used to process the image in some fashion. Finally, a doctor or technician may read the image in order to provide a diagnosis.

The image may capture various details of the subject, which may include bones, organs, tissues, ducts, blood vessels, nerves, previous surgical artifacts such as implants or scar tissue, etc. The image or images may be two-dimensional (i.e., planar) or three-dimensional. In addition, the image capture may produce an image sequence or video that shows live operation, such as a functioning organ, for example. An imaging machine may capture an image, manipulate it, process it in some fashion in order to improve the image, display it to a doctor or technician, and store it for later use.

Computerized image processing generally requires that the image data conform to some sort of protocol, with the protocol being a set of rules and standards that ensure that the information may be efficiently communicated and manipulated among different apparatus. The Digital Imaging and Communications in Medicine (DICOM) standard provides a well-defined and accepted data format and interaction protocol for communicating a processing medical image data, and is incorporated herein by reference. The DICOM standard is available from the Radiological Society of North America, Oak Brook, Ill. 60523-2251.

The DICOM standard has become popular for medical imaging because it ensures that conforming machines can operate on image data communicated from other conforming machines. Machines that may employ the DICOM standard may be workstations, CT scanners, MR images, film digitizers, shared archives (storage devices), printers, and other devices that may be used to process and store image and patient data.

FIG. 1 shows a conventional medical imaging system 100. The medical imaging system 100 may include an imager 107 and imager controller 106 (they may be an integrated device), a patient database 110, an output device 115, a scanner 117, and one or more workstations 122. The imager 107 and imager controller 106 capture an image or images of a patient. The imager 107 may be, for example, a gamma ray camera, an X-ray imager, a magnetic resonance imager (MRI), an ultrasound imager, etc. The patient database 110 may store patient information (i.e., a plurality of records containing a name, vital parameters, a doctor, medical conditions, etc.), and imaging data. The output device 115 may be, for example, a printer, a computer monitor or other display screen, a film developer, etc. The scanner 117 may be a scanning device that digitizes an image. The workstations 122 may be used to access the patient database 110 in order to add or retrieve data. Patient information might also be stored in local databases on the processing workstations. In that case, the patient database 110 acts as a data repository for storage. The various components may be connected by a distributed electronic network 103, such as, for example, a local area network (LAN), a wide area network (WAN), a virtual private network (VPN), or the Internet. The individual components may therefore be located in separate rooms, floors, buildings, or even separate hospitals, clinics or institutions (such as research centers that are not hospitals).

Computerized image processing is well known in the art. However, the need for computing power is ever increasing. For example, recent developments in tomographic reconstruction processes require more and more computing power to more accurately model the physics of image formation. Current processing software memory and processing power requirements may already exceed the specifications of the most powerful computers currently available on the market. As an example, in the field of SPECT imaging, the OSEM 3D reconstruction algorithm currently requires several hours of processing time to process a 256-cube volume, and is therefore not usable in a clinical practice. The processing power requirement is projected to only increase as scanners produce more and more data as resolution and speed increase, and as interest grows in obtaining full resolution co-registered or fused images from different modalities, such as SPECT-CT, PET-CT, SPECT-MRI, etc. Accordingly, there exists a present need in the art to reduce overall radiological image processing time.

SUMMARY OF THE INVENTION

The present invention is provided to solve the above-mentioned problem. According to an aspect of the present invention, there is provided a grid computing system. The grid computing system comprises a software infrastructure, and an imaging device capable of interfacing with the software infrastructure over a distributed electronic network. Also included is a plurality of central processing unit (CPU) workstations capable of interfacing with the software infrastructure over the network. The performance of the plurality of CPUs is dependent on properly balancing load. A large dataset of medical images are split onto several processing nodes of the plurality of CPUs, respectively, such that performance and power is increased.

According to another aspect of the present invention, there is provided a method of grid computing. In the method of the present invention, a grid is limited to a nuclear medicine or radiology network. A tight and easy configuration management of computing nodes, and a tight load balancing between standardized nodes are provided. An existing network of central processing units (CPUs) is utilized, such that the greatest benefit is provided at the lowest cost.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
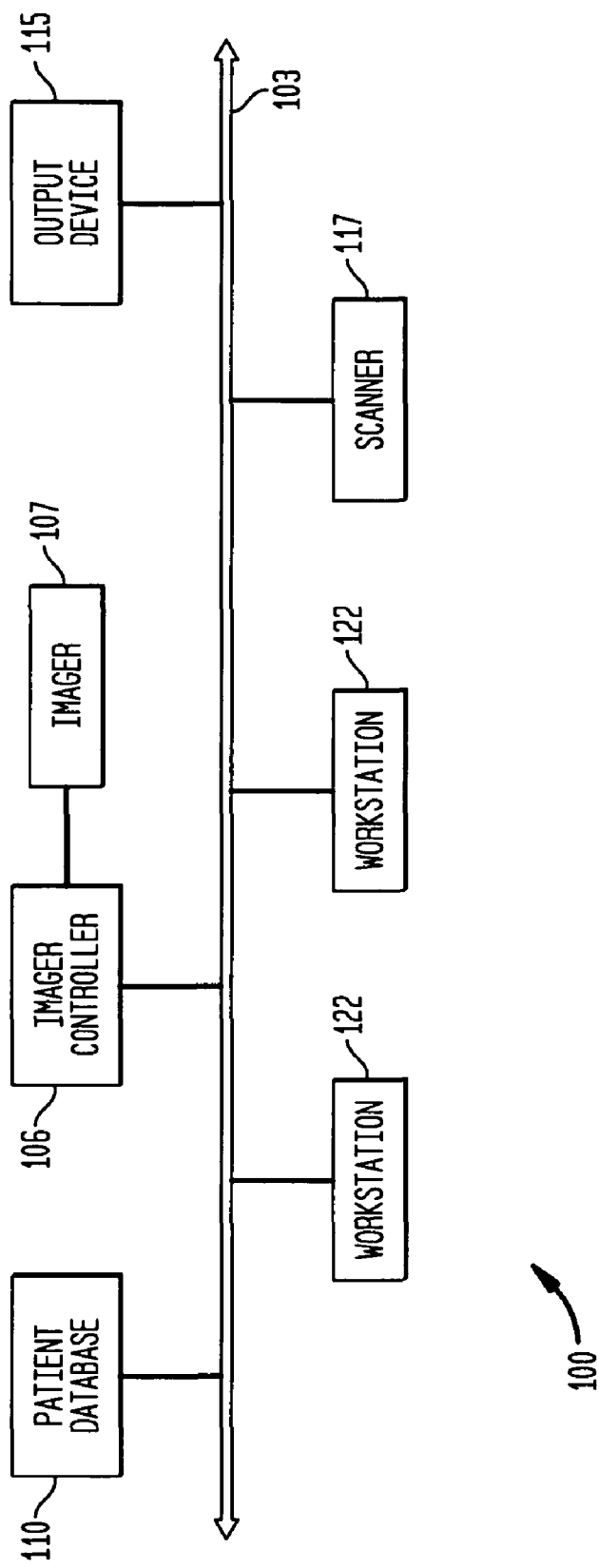
FIG. 1 is a conventional medical imaging system.
Figure 2:
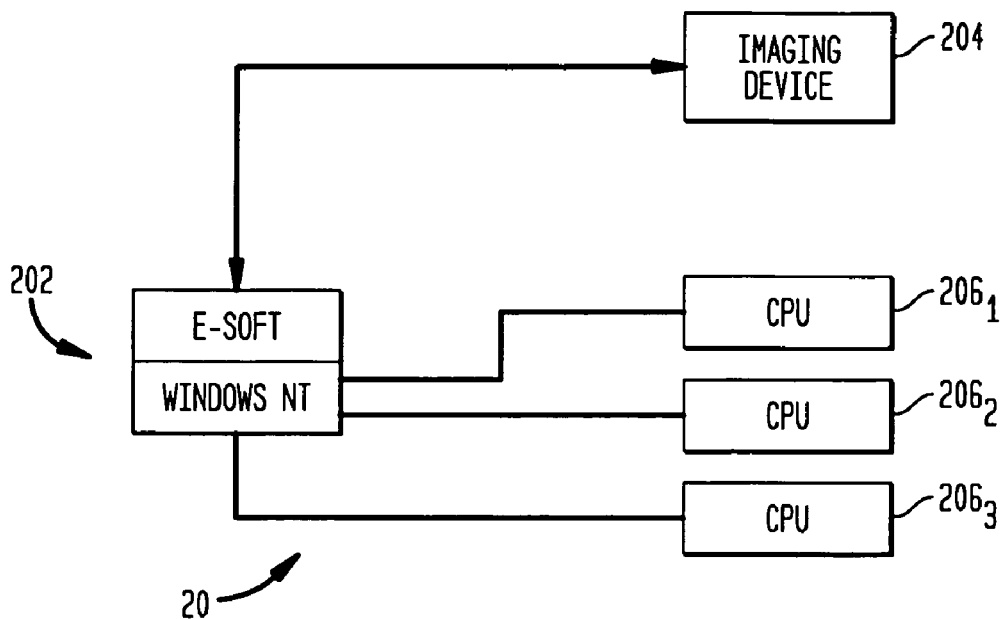
FIG. 2 shows the grid computing system according to an exemplary embodiment of the present invention.

As illustrated in FIG. 2, the grid computing system 20 comprises a master processing workstation 202, an imaging device 204, and a plurality of computing nodes $206_1$-$206_n$. In accordance with the principle of a computing "grid," each workstation is/can be both master and computing node. The imaging device 204 and the plurality of computing nodes $206_1$-$206_n$ interface with the master processing workstation 202 over a network such as, for example, a local area network (LAN), a wide area network (WAN), a virtual private network (VPN), the Internet, or the like.

According to one particular example embodiment of the invention, the master processing workstation 202 may be based on the universally accepted Windows $NT_7$ operating system with a graphical user interface (GUI) that is simple and intuitive. However, the invention is not restricted to any particular operating system or platform, but works on any platform or operation system.

Referring to FIG. 2, the imaging device 204 may be a combined scanning device, such as, for example, positron emission tomography/computed tomography (PET-CT), single photon emission computed tomography/computed tomography (SPECT-CT), or the like. It will be appreciated by those skilled in the art that the imaging device 204 also can be a single imaging device such as, for example, SPECT, planar imaging, or PET or MRI or Ultrasound or any other type of data collecting device.

The plurality of computing nodes $206_1$-$206_n$ can be clusters and networks of workstations interfacing with the master processing workstation 202 over the network, clusters and networks of personal computers interfacing with the master processing workstation 202 over the network, or a combination of clusters and networks of workstations and of personal computers interfacing with the master processing workstation 202 over the network. Accordingly, multimodality images can be viewed on the computing nodes $206_1$-$206_n$ alongside CT, MR, ultrasound, NM, angiography images, or the like. The computing nodes $206_1$-$206_n$ allow access to a universe of information and provide unlimited functionality.

Performance of the plurality of computing nodes $206_1$-$206_n$ is dependent on the ability to balance load, and maintain parallel processing software infrastructure (e.g., versions, updates, software, hardware obsolescence, etc.). In the parallel processing method of the present invention, a large medical dataset is split onto several processing nodes. The acceleration ratios obtained are usually equal to the number of computing nodes.

It is noted that the medical dataset is not limited to images. The benefit of more computing power allows one to consider processing raw information from the scanner before it is actually formatted into images, for example, list mode processing in nuclear medicine carries out processing on count data in the form of a sequential list of numerical values.

When demand processing is performed on the cluster of processing nodes $206_1$-$206_n$, significant and sustainable computer power improvement is achieved (e.g., maximum performance and reliability). Alternatively, when reconstruction load is spread on clusters and networks of workstations and personal computers $206_1$-$206_n$, good performance is achieved. Users such as research sites can mix the workstations and personal computers $206_1$-$206_n$ to achieve the highest demand of computing power.

Figure 3:
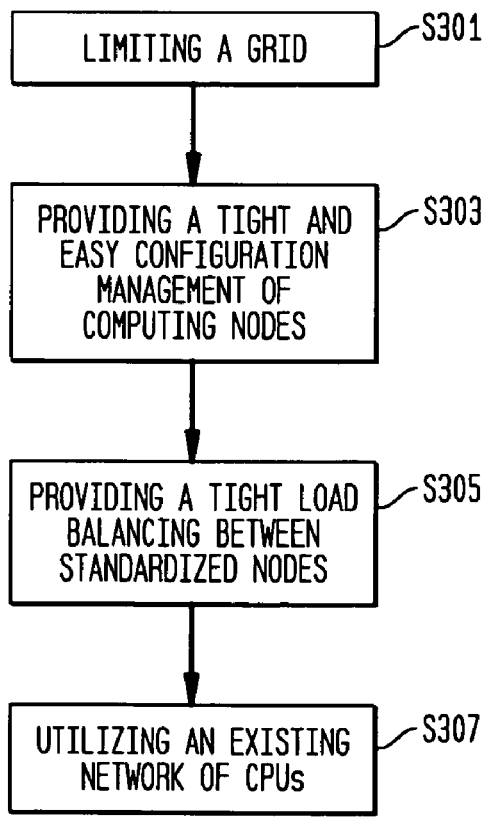
FIG. 3 is a flow chart of the method of grid computing according to an exemplary embodiment of the present invention.

FIG. 3 is a flow chart of a method of grid computing according to an exemplary embodiment of the present invention. In step S301, a network grid is limited to a nuclear medicine or radiology network. This has the beneficial effect of reserving the computing power for those applications that require the most intensive processing. In step S303, a tight and easy configuration management of computing nodes is provided, and a tight load balancing between standardized nodes is also provided (step S305). An existing network of central processing units (CPUs) is utilized in step S307, such that the greatest benefit is provided at the lowest cost (e.g., cycles on idle machines are not wasted).

The grid computing system and method as described herein provide several benefits such as increased performance and power (e.g., maximum performance and reliability).

While a preferred embodiment of the present invention has been described above, it should be understood that it has been presented by way of example only, and not limitation. Thus, the breadth and scope of the present invention should not be limited by the above described exemplary embodiment.

Obviously, numerous modifications and variations of the present invention are possible in light of the above teachings. It is therefore to be understood that the invention may be practiced otherwise than as specifically described herein.

What is claimed:

1. A grid computing system comprising:
   a software infrastructure;
   an imaging device capable of interfacing with said software infrastructure over a distributed electronic network and providing a medical dataset comprising an unprocessed medical image; and
   a plurality of central processing units (CPUs) of a plurality of computing nodes capable of interfacing with said software infrastructure over the network, performance of said plurality of CPUs of a plurality of computing nodes being dependent on balancing a processing load for the medical dataset,
   wherein the medical dataset is split onto said plurality of CPUs of a plurality of computing nodes, respectively, such that obtained acceleration ratios are equal to a number of the plurality of computing nodes, and each of said plurality of CPUs of a plurality of computing nodes performs reconstruction on the received dataset and returns the processed dataset over the software infrastructure network to the imaging device where the split dataset is recombined and displayed.

2. The grid computing system of claim 1, wherein said software infrastructure is based on Windows $NT_7$ operating system with a graphical user interface.

3. The grid computing system of claim 1, wherein said imaging device is a combined imaging apparatus having at least two different imaging modalities.

4. The grid computing system of claim 3, wherein said combined imaging apparatus is a positron emission tomography/or computed tomography (PET-CT) imaging device.

5. The grid computing system of claim 3, wherein said combined imaging apparatus is a single photon emission computed tomography/or computed tomography (SPECT-CT) imaging device.

6. The grid computing system of claim 1, wherein said imaging device is a single scanning device.

7. The grid computing system of claim 6, wherein said single scanning device is a SPECT, PET, single photon planar, or X-ray imaging devices.

8. The grid computing system of claim 1, wherein said plurality of CPUs consists of clusters and networks of workstations.

9. The grid computing system of claim 1, wherein said plurality of CPUs consists of clusters and networks of personal computers.

10. The grid computing system of claim 1, wherein said plurality of CPUs consists of a combination of clusters and networks of workstations and of personal computers.

11. A method of processing medical data, comprising the steps of:
   limiting a computing network grid to a nuclear medicine or radiology network;
   providing a configuration management of computing nodes;
   providing a load balancing between standardized nodes;
   utilizing an existing plurality of central processing units (CPUs) of computing nodes to process nuclear medical image data under said configuration management and load balancing parameters; and
   splitting a medical dataset comprising an unprocessed medical image from a medical imaging device onto several CPUs of the computing nodes, respectively, such that obtained acceleration ratios are equal to a number of the computing nodes, and each of said plurality of CPUs of the computing nodes performs reconstruction on the received dataset and returns the processed dataset over the software infrastructure network to one or more of the standardized nodes where the split dataset is recombined and displayed.

12. The method of claim 11, wherein said network of CPUs consists of clusters and networks of workstations.

13. The method of claim 11, wherein said network of CPUs consists of clusters and networks of personal computers.

14. The method of claim 11, wherein said network of CPUs consists of a combination of clusters and networks of workstations and of personal computers.

15. The method of claim 14, wherein each workstation and personal computer can be both a processing node to serve other workstations, or personal computer in a grid.

* * * * *